(12) United States Patent
Nagy et al.

(10) Patent No.: US 6,228,958 B1
(45) Date of Patent: May 8, 2001

(54) AZABOROLINYL METAL COMPLEXES AS OLEFIN POLYMERIZATION CATALYSTS

(75) Inventors: Sandor Nagy, Grand Island; Ramesh Krishnamurti, Amherst, both of NY (US); Bradley P. Etherton, Houston, TX (US)

(73) Assignee: Equistar Chemicals, L.P., Houston, TX (US)

( * ) Notice: Subject to any disclaimer, the term of this patent is extended or adjusted under 35 U.S.C. 154(b) by 0 days.

(21) Appl. No.: 09/300,370

(22) Filed: Apr. 27, 1999

Related U.S. Application Data

(62) Division of application No. 08/990,416, filed on Nov. 13, 1996, now Pat. No. 5,902,866, which is a continuation of application No. 08/428,384, filed on Apr. 25, 1995, now abandoned.

(51) Int. Cl.$^7$ .................................................. C08F 4/42
(52) U.S. Cl. ...................... 526/134; 526/132; 526/348; 526/348.6; 526/352; 526/133; 502/103; 502/117; 502/162
(58) Field of Search ............................. 502/103, 117, 502/162; 526/132, 133, 134, 348, 348.6, 352

(56) References Cited

U.S. PATENT DOCUMENTS

| | | | |
|---|---|---|---|
| 5,237,069 | 8/1993 | Newman | 526/132 |
| 5,637,659 | 6/1997 | Krishnamurti et al. | 526/132 |

FOREIGN PATENT DOCUMENTS

| | | | |
|---|---|---|---|
| 0 590 486 | * 4/1994 | (EP) . | |
| 590486 | 4/1994 | (EP) . | |
| 916215 | 1/1963 | (GB) . | |
| 1095110 | 4/1989 | (JP) | 526/132 |

OTHER PUBLICATIONS

Gunter Schmidt, et al., "Praparative Und Strukturelle Untersuchunger an η–1, 2–Azaborolinyl–Komplexen des Titans, Vanadins, Eisens und Cobalts," *Chem. Ber.* 115, 3830–3841 (1982).

Gunter Schmid, et al., entitled "Titan–und Vanadiumechlorid–Komplexe mit Diazadiborelidin–und 1, 2–Azaborolinyl– Liganden," *Cehm. Ber.* 118, 2418–2428 (1985).

Joachim Schulze, et al., entitled "1–t–Butyl–2–Methyl–1, 2–Azaborolinyl–Eisen–π–Komplexe," *J. Of Organometallic Chem.* 193, 83–91 (1980).

Roger W. Quan, et al., entitled "Pentamethylcyclopentadienyl Aminoborollide Derivatives of Zirconium and Hafnium: A New Class of Amphoteric Molecule Having Both Lewis Acids and Lewis Base Sites,"*J. Am. Chem. Soc.* 116, 4489–4490 (1994).

* cited by examiner

*Primary Examiner*—David W. Wu
*Assistant Examiner*—Ling-Siu Choi
(74) *Attorney, Agent, or Firm*—Johnathan L. Schuchardt

(57) ABSTRACT

Disclosed is a catalyst having the general formula

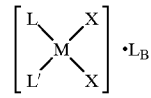

where L is a ligand having the formula

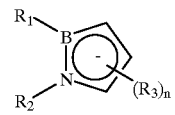

L' is L, Cp, Cp*, indenyl, fluorenyl, $NR_2$, OR, or halogen, L can be bridged to L; X is halogen, $NR_2$, OR, or alkyl from $C_1$ to $C_{12}$, M is zirconium or hafnium, R is alkyl from $C_1$ to $C_{12}$ or aryl from $C_6$ to $C_{12}$, $R_1$ is R, alkaryl from $C_6$ to $C_{12}$, aralkyl from $C_6$ to $C_{12}$, hydrogen, or $Si(R)_3$, $R_2$ is $R_1$, halogen, COR, COOR, SOR, or SOOR, $R_3$ is $R_2$, OR, $N(R)_2$, SR, or a fused ring system, Cp is cyclopentadienyl, Cp* is pentamethylcyclopentadienyl, n is 0 to 3, and $L_B$ is an optional Lewis base. Also disclosed is a method of making a poly-α-olefin comprising polymerizing an α-olefin monomer using a catalyst such as that described above where M can be titanium, zirconium, or hafnium.

12 Claims, No Drawings

AZABOROLINYL METAL COMPLEXES AS OLEFIN POLYMERIZATION CATALYSTS

This application is a divisional application of U.S. patent application Ser. No. 08/990,416, filed on Nov. 13, 1996, now U.S. Pat. No. 5,902,866 which is a continuation of U.S. patent application Ser. No. 08/428,384, filed on Apr. 25, 1995, now abandoned.

BACKGROUND OF THE INVENTION

This invention relates to catalysts useful in homo- and co-polymerizing ethylene and other olefinic hydrocarbons. In particular, it relates to catalysts containing a transition metal π-bonded to a ligand that contains an azaboroline ring.

Until recently, polyolefins have been primarily made with conventional Ziegler catalyst systems. These catalysts typically consist of transition metal-containing compounds and one or more organometallic compound. For example, polyethylene has been made using Ziegler catalysts such as titanium trichloride and diethylaluminum chloride, or a mixture of titanium tetrachloride, vanadium oxytrichloride, and triethylaluminum. These catalysts are inexpensive but they have low activity and therefore must be used at high concentrations. As a result, it is sometimes necessary to remove catalyst residues from the polymer, which adds to production costs. Neutralizing agents and stabilizers must be added to the polymer to overcome the deleterious effects of the catalyst residues. Failure to remove catalyst residues leads to polymers having a yellow or grey color and poor ultraviolet and long term stability. For example, chloride-containing residues can cause corrosion in polymer processing equipment. Furthermore, Ziegler catalysts produce polymers having a broad molecular weight distribution, which is undesirable for some applications such as injection molding. They are also poor at incorporating α-olefin co-monomers. Poor co-monomer incorporation makes it difficult to control the polymer density. Large quantities of excess co-monomer may be required to achieve a certain density and many higher α-olefins, such as 1-octene, may be incorporated at only very low levels, if at all.

Although substantial improvements in Ziegler catalyst systems have occurred since their discovery, these catalysts are now being replaced with the recently discovered metallocene catalyst systems. A metallocene catalyst typically consists of a transition metal compound which has one or more cyclopentadienyl ring ligands. They have low activities when used with organometallic compounds, such as aluminum alkyls, which are used with traditional Ziegler catalysts, but very high activities when used with aluminoxanes as cocatalysts. The activities are generally so high that catalyst residues need not be removed from the polymer. Furthermore, they produce polymers with high molecular weights and narrow molecular weight distributions. They also incorporate α-olefin co-monomers well. However, at higher temperatures metallocene catalysts tend to produce lower molecular weight polymers. Thus, they are useful for gas phase and slurry polymerizations of ethylene, which are conducted at about 80° C. to about 95° C., but they do not generally work well in solution polymerizations of ethylene, at about 150° C. to about 250° C. The polymerization of ethylene in solution is desirable because it allows great flexibility for producing polymers over a wide range of molecular weights and densities as well as the use of a large variety of different co-monomers. One can produce polymers that are useful in many different applications. For example, high molecular weight, high density polyethylene (PE) film useful as a barrier film for food packaging and low density ethylene co-polymers with good toughness and high impact strength.

SUMMARY OF THE INVENTION

We have found a new class of catalysts based on an azaboroline ring structure and containing a transition metal. The catalysts of this invention have unusually high activities, which means that they can be used in very small quantities. They are also very good at incorporating co-monomers into the polymer. They have good activity at higher temperatures and are therefore expected to be useful in solution polymerizations of ethylene.

We have also discovered that the hydrogen response of monomers polymerized with the catalysts of this invention is better than with other catalysts. That is, when the catalysts of this invention are used to polymerize monomers, small variations in the amount of hydrogen present have a large effect on the molecular weight of the resulting polymer.

DESCRIPTION OF THE PREFERRED EMBODIMENTS

The catalysts of this invention have the general formula

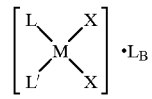

where L is a ligand having the formula

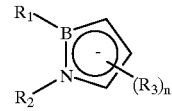

L' is L, Cp, Cp*, indenyl, fluorenyl, $NR_2$, OR, or halogen, L can be bridged to L', X is halogen, $NR_2$, OR, or alkyl from $C_1$ to $C_{12}$, M is titanium, zirconium, or hafnium, R is alkyl from $C_1$ to $C_{12}$ or aryl from $C_6$ to $C_{12}$, $R_1$ is R, alkaryl from $C_6$ to $C_{12}$, aralkyl from $C_6$ to $C_{12}$, hydrogen, or $Si(R)_3$, $R_2$ is $R_1$, halogen, COR, COOR, SOR, or SOOR, $R_3$ is $R_2$, OR, $N(R)_2$, SR, or a fused ring system, Cp is cyclopentadienyl, and Cp* is pentamethylcyclopentadienyl.

The L' ligand is preferably Cp, Cp*, or L as those compounds are easy to make and have good activity. The X group is preferably halogen and most preferably chlorine as those compounds are more readily available. The R group is preferably alkyl from $C_1$, to $C_4$, the $R_1$ group is preferably alkyl from $C_3$ to $C_{12}$ or aryl, the $R_2$ group is preferably t-butyl or trimethylsilyl, and the $R_3$ group is preferably hydrogen or methyl as those compounds are easier to make. Examples of fused ring structures that can be used for $R_3$ include

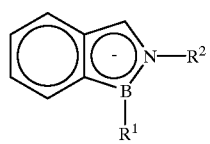

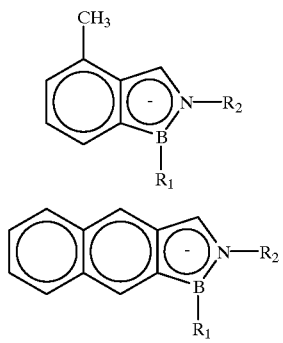

The metal N is preferably zirconium, as the zirconium catalysts offer a good combination of activity and stability.

Optionally, L can be bridged to L'. Groups that can be used to bridged the two ligands include methylene, ethylene, 1,2-phenylene, dimethylsilyl, diphenylsilyl, diethylsilyl, and methylphenylsilyl. Normally, only a single bridge is used in a catalyst. It is believed that bridging the ligands changes the geometry around the catalytically active transition metal and improves the catalyst activity and other properties, such as comonomer incorporation and thermal stability.

In the general formula, $L_B$ is an optional Lewis base. Up to an equimolar amount (with M) of base can be used. The use of the Lewis base is generally not preferred because it tends to decrease catalyst activity. However, it also tends to improve catalyst stability, so its inclusion may be desirable, depending upon the process in which the catalyst is to be used. The base may be residual solvent from the preparation of the azaboroline containing compound or it may be added separately in order to enhance the properties of the catalyst. Examples of bases that can be used in this invention include ethers such as diethylether, dibutylether, tetrahydrofuran, 1,2-dimethoxyethane, esters such as n-butylphthalate, ethylbenzoate, and ethyl p-anisate, tertiary amines such as triethylamine, and phosphines such as triethyl phosphine, tributyl phosphine, and triphenyl phosphine.

The catalysts of this invention can be prepared from commercially available starting materials. Specific starting materials that may not be commercially available can be prepared by techniques well-known in the literature as exemplified by the following. The azaboroline ligand precursor for the catalysts can be prepared from allyl amine by reacting its dianion (generated by a strong base) with an alkyl boron dihalide as described in the literature (J. Schulze, G. Schmid, J. Organomet. Chem., 193, 1980, p. 83).

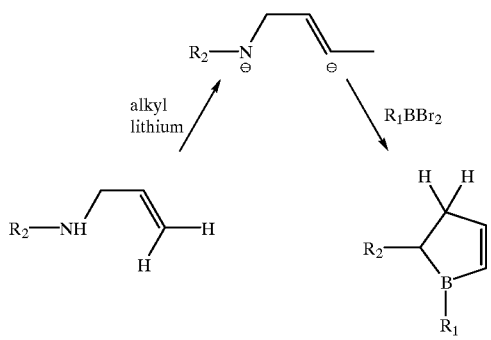

Examples of strong bases that can be used include alkyl lithium compounds such as n-butyl lithium, methyl lithium, and hydrides such as sodium hydride and potassium hydride. Two moles of base are used per mole of the allyl amine. This reaction will occur at room temperature in several hours in a hydrocarbon solvent such as pentane or hexane. Tetramethylethylene diamine in a 1:1 molar ratio with the allyl amine can be used to stabilize the alkyl lithium. The product can be isolated by vacuum and distilled to purify.

In the next step, the product is reacted with a base such as a hindered lithium reagent (e.g., lithium tetramethylpiperidide) to generate the azaborolinyl anion as described in the literature (G. Schmid et al., Chem. Ber., 115, 1982, p. 3830):

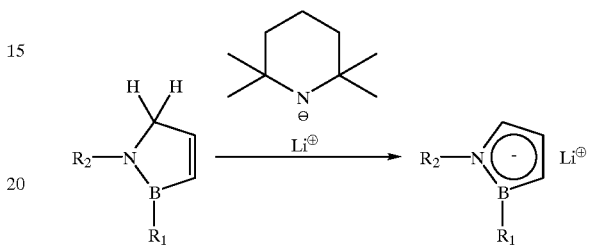

In the final step, the product of the second step is cooled to about −60° C. and $Mx_4$ or $MCpX_3$ is added. The reactants are warmed to room temperature and the reaction is complete when the reactants dissolve and LiX precipitates:

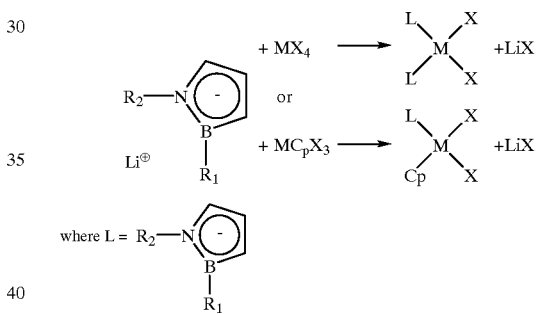

Since the catalyst is normally used in conjunction with an organometallic co-catalyst, it is preferable to dissolve the catalyst in a solvent in which the co-catalyst is also soluble. For example, if methylaluminoxane (MAO) is the co-catalyst then toluene, xylene, benzene, or ethylbenzene could be used as the solvent. Other suitable co-catalysts include aluminum alkyls having the formula $AlR'_x(R_2)_{3-x}$, where $1 \leq x \leq 3$ and $R_2$ is hydrogen, halide, or alkyl or alkoxide from $C_1$ to $C_{20}$, such as triethylaluminum and ethylaluminum dichloride. The preferred co-catalyst is MAO as it results in high activity and a polymer having a narrower molecular weight distribution. The mole ratio of the organometallic co-catalyst to catalyst when used in a polymerization is generally in the range 0.01:1 to 100,000:1, and preferably ranges from 1:1 to 10,000:1.

An alternative co-catalyst is an acid salt that contains a non-coordinating inert anion (see U.S. Pat. No. 5,064,802). The acid salt is generally a non-nucleophilic compound that consists of bulky ligands attached to a boron or aluminum atom, such as lithium tetrakis(pentafluorophenyl) borate, lithium tetrakis(pentafluorophenyl)aluminate, anilinium tetrakis(pentafluorophenyl) borate N,N-dimethylanilinium tetrakis(pentafluorophenyl) borate, trityl tetrakis (pentafluorophenyl) borate, and mixtures thereof. The anion which results when these compounds, react with the catalyst is believed to be weakly coordinated to the metal-containing cation. The mole ratio of acid salt to catalyst can range from about 0.01:1 to about 1000:1, but is preferably about 1:1 to 10:1. While there is no limitation on the method of preparing an active catalyst system from the catalyst and the acid salt, preferably they are mixed in an inert solvent at temperatures in the range of about −78° C. to about 150° C. They can also be mixed in the presence of monomer if desired. The acid salt can be used in combination with the organometallic cocatalysts described earlier.

The catalyst and co-catalyst can be used on a support such as silica gel, alumina, silica, magnesia, or titania, but supports are not preferred as they may leave contaminants in the polymer. However, a support may be required depending upon the process being utilized. For example, a support is generally needed in gas phase polymerization processes and slurry polymerization processes in order to control the particle size of the polymer being produced and in order to prevent fouling of the reactor walls. The support may also increase the thermal stability of the catalyst. To use a support, the catalyst and co-catalyst are dissolved in the solvent and are precipitated onto the support material by, for example, evaporating the solvent. The co-catalyst can also be deposited on the support or it can be introduced into the reactor separately from the supported catalyst.

Once the catalyst has been prepared it should be used as promptly as possible as it may lose some activity during storage. Storage of the catalyst should be at a low temperature, such as −100 to about 20° C. The catalyst is used in a conventional manner in the polymerization of olefinic hydrocarbon monomers. While unsaturated monomers such as styrene can be polymerized using the catalysts of this invention, it is particularly useful for polymerizing α-olefins such as propylene, 1-butylene, 1-hexene, 1-octene, and especially ethylene.

The catalyst is also useful in a conventional manner for copolymerizing mixtures of unsaturated monomers such as ethylene, propylene, 1-butene, 1-hexene, 1-octene, and the like; mixtures of ethylene and di-olefins such as 1,3-butadiene, 1,4-hexadiene, 1,5-hexadiene, and the like; and mixtures of ethylene and unsaturated comonomers such as norbornene, ethylidene norbornene, vinyl norbornene, norbornadiene, and the like.

The catalysts of this invention can be utilized in a variety of different polymerization processes. They can be utilized in a liquid phase polymerization process (slurry, solution, suspension, bulk phase, or a combination of these), in a high pressure fluid phase, or in a gas phase polymerization process. The processes can be used in series or as individual single processes. The pressure in the polymerization reaction zones can range from about 15 psia to about 50,000 psia and the temperature can range from about −100° C. to about 300° C.

The following examples further illustrate this invention.

EXAMPLE 1

Preparation of Bis(1-tert-butyl-2-methyl-$\eta^5$-1,2-azaborolinyl)zirconium dichloride and 1-tert-butyl-2-methyl-$\eta^5$-1,2-azaborolinyl)zirconium trichloride 2-Methyl-1-tert-butyl-1,2-azaborolinyllithium was prepared by adding a solution of 0.438 g (3.2 mmol) of 2-methyl-1-tert-butyl-$\Delta^3$-1,2-azaboroline (prepared according to the literature procedure: J. Schultze and G. Schmid, *J. Organomet. Chem.*, 1980, 193, 83–91) in 6 mL of dry THF to a cold (−78° C.) solution of lithium 2,2,6,6-tetramethylpiperidide (3.2 mmol) which had been prepared by reaction of equimolar amounts of 2,2,6,6-tetramethylpiperidine and n-butyllithium/hexanes in 10 mL THF. The cold bath was allowed to warm up to 10° C. over 1.5 hours after which the solvents were removed under vacuum. The yellow oily residue was treated with 35 mL toluene to give a yellow slurry. This was cooled to −60° C. and zirconium (IV) chloride (0.37 g, 1.6 mmol) was added with good stirring. The bath was warmed to room temperature and the mixture stirred overnight. The solvent was evaporated under vacuum and residue was treated with 30 mL toluene and lithium chloride filtered off. The toluene filtrate was concentrated and the sticky yellow residue was extracted with hexane (2×15 mL) and filtered. Evaporation of hexane filtrate gave 0.14 g of a yellow solid. $^1$H NMR spectrum of the material showed it to be a ca. ⅔ mixture of the two desired compounds.

EXAMPLE 2

Preparation of ($\eta^5$-cyclopentadienyl) (1-tert-butyl-2-methyl-$\eta^5$-1,2-azaborolinyl)zirconium dichloride

METHOD A

A solution of 2-methyl-1-tert-butyl-1,2-azaborolinyllithium prepared from 2-methyl-1-tert-butyl-$\Delta^3$-1,2-azaboroline (0.49 g, 3.5 mmol) in 20 mL THF as described above, was added dropwise via syringe to a stirred cold (−35° C.) solution of cyclopentadienylzirconium trichloride (0.93 g, 3.52 mmol) in 50 mL THF. The bath was allowed to warm to room temperature and the mixture stirred overnight. The solvents were evaporated in vacuo and residue extracted with 35 mL toluene and filtered. The precipitate was washed with 10 mL toluene and the combined filtrate was evaporated. The resulting gummy residue was stirred with 25 mL dry hexane which produced a beige solid and a pale yellow-supernatant. The mixture was filtered and the solid dried to give 0.77 g of product as a tan-colored amorphous powder. $^1$H NMR spectrum of the material indicated it to be desired product contaminated with some impurities.

METHOD B

2-Methyl-1-tert-butyl-1,2-azaborolinyllithium was prepared by adding a solution of 0.438 g (3.2 mmol) of 2-methyl-1-tert-butyl-$\Delta^3$-1,2-azaboroline (prepared according to the literature procedure: J. Schultze and G. Schmid, J. Organomet. Chem., 1980, 193, 83–91) in 10 mL of dry toluene to a cold (−78° C.) solution of lithium 2,2,6,6-tetramethylpiperidide (3.2 mmol; prepared by reaction of equimolar amounts of 2,2,6,6-tetramethylpiperidine and n-butyllithium/hexanes in 15 mL THF). The solvents were evaporated in vacuo to one-third the initial volume, the solution was cooled to −78° C. and 35 mL dry toluene was added. The clear yellow solution was stirred well while cyclopentadienylzirconium trichloride (0.84 g, 3.2 mmol) was added via transfer tube. The bath was warmed to room temperature and stirred overnight. The reaction mixture was filtered, and filtrate evaporated to dryness. To the solid residue was added 20 mL toluene and the mixture was filtered to remove a dark insoluble material from a yellow filtrate. The filtrate was concentrated to give 0.34 g of a yellow amorphous powder whose $^1$H NMR spectrum indicated it to be the desired product.

EXAMPLES 3 TO 11

Polymerization of Ethylene With Azaborolinylzirconium Catalysts

The ethylene was polymerized using the catalyst prepared according to Method 2A. The polymerizations were conducted in a stirred 1.7 liter autoclave at 80 to 110° C. Dry, oxygen-free toluene (840 ml) was charged to a clean, dry, oxygen-free reactor. MAO from Ethyl Corporation (10 wt % in toluene) was used in the polymerizations. The desired amount of MAO to give the ratio shown in the table which follows was added by syringe at 30° C. The reactor was heated to the desired temperature and sufficient ethylene was added to bring the reactor pressure to 150 psig. The reactor was allowed to equilibrate at the desired temperature and pressure. A solution of catalyst was prepared by dissolving 0.100 grams of product in 100 ml of toluene. The co-catalyst was injected into the reactor first and the catalyst was injected separately. The amount of this solution needed to give the amount of catalyst shown in the table was used to start a polymerization. Ethylene flowed into the reactor as needed in order to keep the pressure constant at 150 psig as polymer was produced.

At the end of 1 hour (less, if the activity was very high) the ethylene flow was stopped and the reactor was rapidly cooled to room temperature. The reactor was opened and the polymer was filtered from the toluene. The product was dried overnight in a vacuum oven and weighed. Table 1 gives the reaction conditions and Table 2 gives the results of polymerizations.

TABLE 1

| Example | Catalyst Amount (mmoles) | MAO Amount (mmoles) | Al/TM | T (° C.) | H2 Amount (mmoles) | Butene Amount (ml) | Run Time (hr) |
|---|---|---|---|---|---|---|---|
| 3  | 0.00552 | 9.0  | 1630 | 80  | 0  | 0  | 0.5 |
| 4  | 0.00138 | 2.25 | 1630 | 80  | 0  | 0  | 0.5 |
| 5  | 0.00138 | 4.5  | 3261 | 80  | 0  | 0  | 0.5 |
| 6  | 0.00138 | 4.5  | 3261 | 80  | 30 | 0  | 1 |
| 7  | 0.00138 | 4.5  | 3261 | 80  | 30 | 20 | 1 |
| 8  | 0.00276 | 4.5  | 1630 | 110 | 0  | 0  | 1 |
| 9  | 0.00276 | 9    | 3261 | 110 | 0  | 0  | 1 |
| 10 | 0.00276 | 9    | 3261 | 110 | 30 | 0  | 1 |
| 11 | 0.00276 | 9    | 3261 | 110 | 30 | 20 | 1 |

TABLE 2

| Example | Polymer Wt (g) | Productivity (kg/g Zr/hr) | MI2 (dg/min) | MFR | Density (g/ml) | Mw/Mn |
|---|---|---|---|---|---|---|
| 3  | 61.8 | 245 | 0.16  | 17.0 | 0.9577 | — |
| 4  | 42.2 | 670 | 0.03  | 24.2 | 0.9500 | — |
| 5  | 43.2 | 686 | 0.04  | 21.3 | 0.9529 | 1.79 |
| 6  | 71.2 | 566 | 4.29  | 28.7 | 0.9669 | — |
| 7  | 85.4 | 678 | 3.44  | 25.9 | 0.9503 | 5.14 |
| 8  | 62.2 | 247 | 0.92  | 22.1 | 0.9589 | — |
| 9  | 67.3 | 267 | 1.40  | 15.1 | 0.9622 | 1.74 |
| 10 | 80.5 | 320 | 3.56  | 21.7 | 0.9660 | — |
| 11 | 93.7 | 372 | 11.56 | 21.7 | 0.9483 | 3.73 |

The above table shows that polymers having a wide range of molecular weights can be made using the catalysts of this invention because the catalysts are more sensitive to hydrogen.

The melt index of the polymer was measured according to ASTM D-1238, Condition E and Condition F. MI2 is the melt index measured with a 2.16 kg weight (Condition E). MI20 is the melt index measured with a 21.6 kg weight (Condition F). MFR is the ratio of MI20 to MI2. The polymer density was measured according to ASTM D-1505. The molecular weight distribution of the polymer was measured using a Waters 150C gel permeation chromatograph at 135° C. with 1,2,4-trichlorobenzene as the solvent. Both weight average molecular weight ($M_w$) and ratio of $M_w$ to $M_n$ (number average molecular weight) were used to characterize the molecular weight distribution.

EXAMPLES 12 AND 13

Solution polymerizations were conducted in a stirred 2.0 liter stainless steel autoclave at 150° C. 1.0 liter of dry, oxygen-free Isopar® G (from Exxon Chemical Company) was charged to the clean, dry, oxygen-free reactor. The reactor was then allowed to equilibrate at 150° C. It was pressured with sufficient ethylene to give an ethylene partial pressure of 150 psig. No hydrogen or co-monomer were added. A solution of catalyst described in Example 2 was mixed with a solution containing 10% methylaluminumoxane (MAO) in toluene (from Albemarle Corporation and used without further purification). This mixture was stirred for 15 minutes. 10.0 ml of this mixture was injected into the reactor to start the polymerization. The amount of catalyst and MAO in the 10.0 ml is shown in Table 3 along with the experimental conditions. Ethylene was fed to the reactor in order to keep the pressure constant.

At the end of 15 minutes the ethylene flow was stopped and the reaction mixture was transferred to a vessel containing a solution of an antioxidant in Isopar® G The solution was cooled to room temperature overnight. The polymer was filtered from the solvent by vacuum filtration. It was dried overnight in a vacuum oven and weighed. The weight of the polymer was 12.1 grams. The polymer MI2 was 118 dg/min. Additional polymer properties are shown in Table 2.

EXAMPLES 14 TO 18

Slurry polymerization were conducted in a manner identical to that described in Examples 3 through 11. The catalyst described in Example 1 was used in those polymerizations. The polymerization conditions are shown in Table 3. The properties of the polymers which were produced are shown in Table 4.

TABLE 3

| Example | Catalyst Amount (mmoles) | MAO Amount (mmoles) | Al/TM | T (° C.) | H2 Amount (mmoles) | Butene Amount (ml) | Run Time (hr) |
|---|---|---|---|---|---|---|---|
| 12 | 0.0138 | 7.5 | 543 | 150 | 0 | 0 | 0.25 |
| 13 | 0.0138 | 3.8 | 272 | 150 | 0 | 0 | 0.25 |
| 14 | 0.00552 | 9.0 | 1630 | 80 | 0 | 0 | 1.0 |
| 15 | 0.00552 | 13.5 | 2446 | 80 | 0 | 0 | 1.0 |
| 16 | 0.00552 | 13.5 | 2446 | 110 | 0 | 0 | 1.0 |
| 17 | 0.00552 | 13.5 | 2446 | 110 | 30 | 0 | 1.0 |
| 18 | 0.00552 | 13.5 | 2446 | 110 | 30 | 20 | 1.0 |

TABLE 4

| Example | Polymer Wt (g) | Productivity (kg/g Zr/hr) | MI2 (dg/min) | MFR | Density (g/ml) |
|---|---|---|---|---|---|
| 12 | 12.1 | 38 | 118 | 23 | 0.9660 |
| 13 | 8.8 | 28 | 108 | 25 | 0.9483 |
| 14 | 50.9 | 101 | 0.04 | 18.3 | 0.9609 |
| 15 | 49.0 | 97 | 0.06 | 15.0 | 0.9714 |
| 16 | 39.7 | 79 | 203 | — | >0.9700 |
| 17 | 34.0 | 68 | 111 | 24.9 | >0.9700 |
| 18 | 42.2 | 84 | 166 | 16.7 | >0.9700 |

The above table shows that the catalyst has good activity and can produce polymer with very high crystallinity and density. The low MFR values indicate that the polymer has a narrow molecular weight distribution.

What is claimed is:

1. A catalyst comprising a component having the general formula:

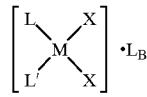

where L is a ligand having the formula

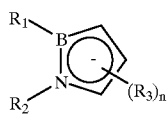

L' is cyclopentadienyl, pentamethylcyclopentadienyl, indenyl, fluorenyl, $NR_2$, OR, or halogen, L' can be bridged to L, X is halogen, $NR_2$, OR, or alkyl from $C_1$ to $C_{12}$, M is zirconium, titanium, or hafnium, R is alkyl from $C_1$ to $C_{12}$ or aryl from $C_6$ to $C_{12}$, $R_1$ is R, $Si(R)_3$, or $R_4$, $R_4$ is alkayl from $C_6$ to $C_{12}$, aralkyl from $C_6$ to $C_{12}$, or hydrogen, $R_2$ is R, $R_4$, halogen, COR, COOR, SOR, or SOOR, $R_3$ is $R_2$, $Si(R)_3$ OR, $N(R)_2$, SR, or a fused ring system, n is 0 to 3, and $L_B$ is an optional Lewis base; and an alumoxane cocatalyst.

2. The catalyst of claim 1, wherein L' is cyclopentadienyl.

3. The catalyst of claim 1, wherein both X are chlorine.

4. The catalyst of claim 1, wherein $R_3$ is $Si(R)_3$.

5. The catalyst of claim 1, wherein $R_1$ and $R_2$ are independently $C_1$–$C_6$ alkyl groups.

6. The catalyst of claim 1, wherein $R_1$ and $R_2$ of both L and L' are independently $C_1$–$C_6$ alkyl groups.

7. The catalyst of claim 5, wherein each X is chlorine.

8. The catalyst of claim 6, wherein each X is both chlorine.

9. The catalyst of claim 1, wherein M is zirconium.

10. The catalyst of claim 5, wherein M is zirconium.

11. A catalyst according to claim 1 which is 1-tert-butyl-2-methyl-$\eta^5$-1,2-azaborolinyl)zirconium trichloride.

12. A catalyst comprising a component having the general formula:

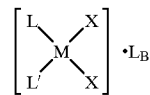

where L is a ligand having the formula

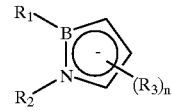

L' is L, cyclopentadienyl, pentamethylcyclopentadienyl, indenyl, fluorenyl, $NR_2$, OR, or halogen, L can be bridged to L'; X is halogen, $NR_2$, OR, or alkyl from $C_1$ to $C_{12}$, M is titanium, zirconium or hafnium; R is alkyl from $C_1$ to $C_{12}$ or aryl from $C_6$ to $C_{12}$; $R_1$ is a $C_6$ to $C_{12}$ aryl group, a $C_6$ to $C_{12}$ alkaryl group, a $C_6$ to $C_{12}$ aralkyl group, hydrogen or $Si(R)_3$; $R_2$ is $R_1$, a $C_1$ to $C_{12}$ alkyl group, halogen, COR, COOR, SOR, or SOOR; $R_3$ is $R_2$, OR, $N(R)_2$, SR, or a fused ring system; n is 0 to 3 and $L_B$ is an optional Lewis base; and an alumoxane cocatalyst.

* * * * *